United States Patent [19]

Sakai et al.

[11] Patent Number: 4,713,454
[45] Date of Patent: Dec. 15, 1987

[54] PREPARATION PROCESS OF (6R)-TETRAHYDRO-L-BIOPTERIN

[75] Inventors: Hideaki Sakai, Yokohama; Tadashi Kanai, Chiba, both of Japan

[73] Assignees: Shiratori Pharmaceutical Co., Ltd., Narashino; Suntory Limited, Osaka, both of Japan

[21] Appl. No.: 824,288

[22] Filed: Jan. 23, 1986

[30] Foreign Application Priority Data

Jan. 28, 1985 [JP] Japan .................................. 60-12477
Jan. 28, 1985 [JP] Japan .................................. 60-12478

[51] Int. Cl.⁴ .............................................. C07D 475/04
[52] U.S. Cl. ...................................... 544/258; 260/690
[58] Field of Search ............................ 544/258; 260/690

[56] References Cited

U.S. PATENT DOCUMENTS 4,595,752  6/1986  Azuma .................................. 544/258

*Primary Examiner*—Donald G. Daus
*Assistant Examiner*—Mark W. Noel
*Attorney, Agent, or Firm*—Oblon, Fisher, Spivak, McClelland, & Maier

[57] ABSTRACT (6R)-Tetrahydro-L-biopterin of the following formula:

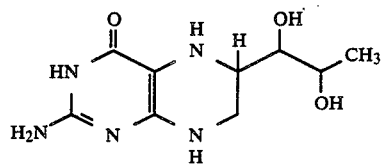

is prepared by catalytically reducing L-erythrobiopterin or an acyl derivative thereof in the presence of an amine, at pH 10–13 and with a platinum-base catalyst and when one or more acyl groups still remain, then removing the acyl groups. (6R)-Tetrahydro-L-biopterin is effective for the treatment of certain serious neuroses and malignant hyperphenylalaniemia. The present invention has succeeded in preparing (6R)-tetrahydro-L-biopterin at a high asymmetric ration R/S and moreover with a high yield. Since the process of this invention makes use of an amine as a base, the process is free from admixture of any inorganic salt and can hence provide high-purity crystals with ease.

11 Claims, No Drawings

PREPARATION PROCESS OF (6R)-TETRAHYDRO-L-BIOPTERIN

BACKGROUND OF THE INVENTIION

1. Field of the Invention

This invention relates to a process for the preparation of (6R)-tetrahydro-L-biopterin represented by the following general formula (I):

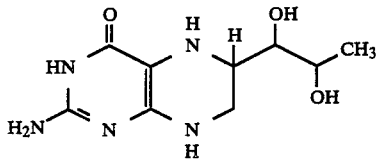

more specifically to an industrial preparation process which can provide the 6R form of tetrahydro-L-biopterin in a high proportion.

DISCUSSION OF THE BACKGROUND

Tetrahydro-L-biopterin (hereinafter abbreviated as "$BPH_4$") contains two isomers, i.e., the 6R and 6S forms depending on the steric configuration of hydrogen at the 6-position [Furrer, H. J., et al.: Helv. Chim. Acta. 62, 2577(1979)].

Of the two stereoisomers, (6R)-$BPH_4$ is a coenzyme not only for phenylalanine hydroxylases but also for aromatic amino acid hydroxylases.

Its shortage thus leads to scarceness in neurotransmitters such as serotonin, dopamine, noradrenalin and adrenalin, thereby inducing serious neuroses. Malignant hyperphenylalaninemia is a serious and incurable disease which is one of inborn errors of metabolism and cannot be easily treated by any conventional pharmacotherapy. This disease is also known to occur as a result of inhibition of conversion of phenylalanine to tyrosine due to scarceness of (6R)-$BPH_4$.

It may be contemplated to administer (6R)-$BPH_4$ for the treatment of malignant hyperphenylalaninemia. For this application, it has been desired to develop a process for economical preparation of this compound with high purity.

As preparation processes of tetrahydro-L-biopterin, it has been known to reduce L-erythrobiopterin enzymatically or chemically. Of these processes, the enzymatic process is unavoidably accompanied by such a drawback that it requires complex facilities and operation, results in a high preparation cost and is hence disadvantageous as an industrial process, although it has a merit that it provides the 6R form only. On the other hand, the chemical process yields a mixture of the 6R form and 6S form, which must be separated subsequently. This separation is however extremely difficult to achieve. No effective method has heretofore been known for their separation.

Accordingly, it has long been desired to develop a process for synthesizing (6R)-$BPH_4$ in a high proportion, if possible, selectively. However, no satisfactory process has yet been found.

SUMMARY OF THE INVENTION

With the foregoing circumstances in view, the present inventor have carried out an extensive research. As a result, it has been found that the asymmetric ratio R/S can be significantly increased by subjecting L-erythrobiopterin or an acyl derivative thereof to catalytic reduction by a platinum-based catalyst, in the presence of an amine and under specific conditions and moreover, the resultant reaction mixture having such a high R/S ratio facilitates the separation and collection of (6R)-$BPH_4$, leading to completion of the present invention.

Accordingly, this invention provides a process for the preparation of (6R)-tetrahydro-L-biopterin (I), which comprises catalytically reducing L-erythrobiopterin or an acyl derivative thereof (II) in the presence of an amine, at pH 10–13 and with a platinum-based catalyst and when one or more acyl groups still remain, then removing the acyl groups.

The present invention has succeeded in preparing (6R)-$BPH_4$, the chemical synthesis of which has heretofore been difficult, at a high asymmetric ratio R/S and moreover with a high yield, and is hence an extremely valuable invention.

Since the process of this invention makes use of an amine as a base, the process is free from admixture of any inorganic salt and can hence provide high-purity crystals with ease. This is another advantageous feature of this invention.

The above and other objects, features and advantages of the present invention will become apparent from the following description and the appended claims.

DETAILED DESCRIPTION OF THE INVENTION AND PREFERRED EMBODIMENTS

The reaction of the above process is represented by the following equation:

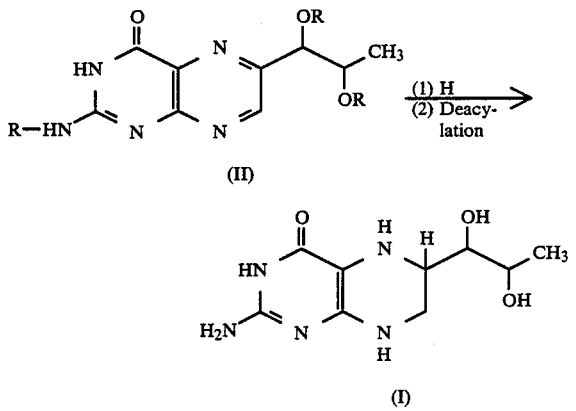

wherein R means H or acyl group.

In order to practice the present invention, L-erythrobiopterin or its acyl derivative (II) is catalytically reduced with a platinum-based catalyst in water, an alcohol or a mixed water-alcohol solvent, which has in advance been adjusted to pH 10–13 with an amine.

As the platinum-based catalyst, may for example be mentioned platinum black, platinum oxide ($PtO_2$), platinum/carbon (Pt/C), platinum/alumina (Pt/alumina) or the like. Of these, platinum black is particularly preferred in view of yield and asymmetric ratio. On the other hand, illustrative of the alcohol may include methanol, ethanol, methyl cellosolve, ethylene glycol and so on.

As exemplary amines, may be mentioned primary amines such as methylamine, ethylamine, propylamine and cyclohexylamine; secondary amines such as dimethylamine, diethylamine, dipropylamine, piperidine and morpholine; tertiary amines such as trimethylamine, triethylamine and tripropylamine; and quaternary amines such as tetramethylammonium hydroxide, tetraethylammonium hydroxide and tetrapropylammonium hydroxide. These amines may each be added in such an amount that the pH of the resulting reaction solution reaches pH 10–13. The presence of such an amine is essential in the present invention. Even if the pH is adjusted to the above-described range by using another base, for example, an inorganic base such as an alkali metal hydroxide, the asymmetric ratio R/S will be low and the yield will also be poor.

The process of this invention may be carried out in accordance with a usual procedure for catalytic reduction. The reaction temperature may preferably be $-10°$ C. to 50° C., while the $H_2$ pressure may be preferably 1 kg/cm$^2$ or higher with 10 to 100 kg/cm$^2$ being especially preferred.

In the above manner, (6R)-BPH$_4$ or its acyl derivative can be obtained with an asymmetric ratio of about 7 or greater. The acyl group or groups are usually removed in the above-described reaction. When some of the acyl groups still remain, they can be removed with ease by hydrolyzing the reaction product with hydrochloric acid or the like. By recrystallizing the thus-obtained reaction product, (6R)-BPH$_4$ can be isolated and obtained with high purity.

Having generally described this invention, a further understanding can be obtained by reference to certain specific examples which are provided herein for purpose of illustration only and are not intended to be limiting unless otherwise specified.

EXAMPLE 1

To 95 ml of water were added 1.0 g (4.22 mmol) of L-erythro-biopterin and 0.20 g of platinum black, followed by an addition of 10% tetraethylammonium hydroxide to adjust the resultant mixture to pH 12.0. Thus thus-prepared mixture was charged in an autoclave and reacted with stirring, at an $H_2$ pressure of 100 kg/cm$^2$, temperature of 0°–5° C. and revolution rate of 1000 r.p.m. for 20 hours. To the reaction mixture was added 5 ml of concentrated hydrochloric acid, followed by removal of the catalyst through filtration. The filtrate was then concentrated under reduced pressure at a bath temperature not higher than 35° C. The residue was recrystallized from a mixed solvent of 3N hydrochloric acid and ethanol.

White crystals, (6R)-BPH$_4$.2HCl were obtained in an amount of 1.13 g (yield: 85%).

Elemental analysis: Calculated for C$_9$H$_{17}$Cl$_2$N$_5$O$_3$: C, 34.41; H, 5.45; N, 22.29. Found: C, 34.50; H, 5.41; N, 22.58.

Optical rotation $[\alpha]_D^{25}$: $-6.39°$ (C, 0.68; 0.1N HCl)

$^1$H-NMR (CD$_3$OD+D$_2$O): 4.10–3.70 (5H, m, H-C(6,7,1',2')), 1.40 (3H, d, J=6 Hz, H-C(3')).

EXAMPLE 2

To 95 ml of water were added 1.0 g (4.22 mmol) of L-erythro-biopterin and 0.20 g of platinum black, followed by an addition of each of the bases shown in Table 1 to adjust the resultant mixture to a prescribed pH level. The thus-prepared mixture was charged in an autoclave and reacted with stirring, at an $H_2$ pressure of 100 kg/cm$^2$, temperature of 0° to 5° C. and revolution rate of 1000 r.p.m. and for 20 hours. The reaction mixture was added with 5 ml of concentrated hydrochloric acid, followed by removal of the catalyst through filtration. The filtrate was then analyzed by high-pressure liquid chromatography to determine the corresponding R/S ratio and the yield of (the R form+the S form). Results are summarized in Table 1.

Conditions for measurement by high-pressure liquid chromatography:

Detector: ultraviolet absorption photometer (measurement wavelength: 275 nm)

Column: Partisil-10SCX, 4.5×250 mm

Mobile phase: 30 mM ammonium phosphate plus 3 mM ammonium sulfite (pH=3.0)

Flow rate: 2 ml/min.

TABLE 1

| Base | pH | R/S | Yield of R + S forms |
|---|---|---|---|
| Ammonia | 11.03 | 8.2 | 75 |
| Methylamine | 12.24 | 12.0 | 81 |
| Ethylamine | 11.98 | 14.3 | 91 |
| Diethylamine | 11.99 | 8.3 | 70 |
| Trimethylamine | 10.82 | 9.7 | 91 |
| Triethylamine | 12.01 | 19.0 | 95 |
| Triethylamine | 12.37 | 22.0 | 89 |
| Tetramethylammonium hydroxide | 12.02 | 14.8 | 93 |
| Tetraethylammonium* hydroxide | 12.02 | 19.0 | 95 |
| Benzyltrimethylammonium hydroxide | 12.16 | 15.3 | 95 |
| Cyclohexylamine | 12.29 | 7.7 | 96 |
| Piperidine | 12.05 | 10.8 | 78 |
| Morpholine | 10.31 | 7.9 | 96 |

*Example 1

EXAMPLE 3

The procedure of Example 2 was repeated except that the pH of the starting reaction solution was changed to pH 12 by using triethylamine, diethylamine, ethylamine and tetraethylammonium hydroxide respectively and the reaction temperature and $H_2$ pressure were changed. Results are shown in Table 2–Table 5.

TABLE 2

| | Base Triethylamine (pH = 12.0) $H_2$ pressure | | | | | |
|---|---|---|---|---|---|---|
| | 1 kg/cm$^2$ | | 20 kg/cm$^2$ | | 100 kg/cm$^2$ | |
| Temperature | R/S | (R + S forms) yield (%) | R/S | (R + S forms) yield (%) | R/S | (R + S forms) yield (%) |
| 0–5° C. | 7.6 | 88 | 12.0 | 94 | 18.5 | 94 |
| 20° C. | 5.9 | 97 | 10.2 | 93 | 16.4 | 94 |
| 40° C. | 5.5 | 93 | 10.6 | 88 | 11.3 | 89 |

TABLE 3

| | Base Diethylamine (pH = 12.0) $H_2$ pressure | | | | | |
|---|---|---|---|---|---|---|
| | 1 kg/cm$^2$ | | 20 kg/cm$^2$ | | 100 kg/cm$^2$ | |
| Temperature | R/S | (R + S forms) yield (%) | R/S | (R + S forms) yield (%) | R/S | (R + S forms) yield (%) |
| 0–5° C. | 7.4 | 86 | 10.9 | 96 | 14.9 | 93 |
| 20° C. | 6.5 | 95 | 9.7 | 94 | 12.8 | 90 |
| 40° C. | 5.3 | 87 | 8.5 | 88 | 11.3 | 89 |

TABLE 4

| | Base Ethylamine (pH = 12.0) H₂ pressure | | | | | |
|---|---|---|---|---|---|---|
| | 1 kg/cm² | | 20 kg/cm² | | 100 kg/cm² | |
| Temperature | R/S | (R + S forms) yield (%) | R/S | (R + S forms) yield (%) | R/S | (R + S forms) yield (%) |
| 0–5° C. | 5.5 | 67 | 12.1 | 96 | 14.3 | 91 |
| 20° C. | 8.4 | 97 | 10.9 | 96 | 13.0 | 96 |
| 40° C. | 6.7 | 95 | 10.1 | 88 | 11.4 | 87 |

TABLE 5

| | Base Tetraethylammonium hydroxide (pH = 12.0) H₂ pressure | | | | | |
|---|---|---|---|---|---|---|
| | 1 kg/cm² | | 20 kg/cm² | | 100 kg/cm² | |
| Temperature | R/S | (R + S forms) yield (%) | R/S | (R + S forms) yield (%) | R/S | (R + S forms) yield (%) |
| 0–5° C. | 7.2 | 86 | 10.7 | 93 | 14.5 | 95 |
| 20° C. | 6.4 | 96 | 9.6 | 95 | 13.4 | 94 |
| 40° C. | 5.6 | 87 | 12.4 | 86 | 10.3 | 92 |

EXAMPLE 4

To 2 ml of each of the solvents shown in Table 6 were added 20 mg of L-erythro-biopterin and 4 mg of platinum black, followed by an addition of the corresponding base given in Table 6 to adjust the resultant mixture to a prescribed pH level. The thus-prepared mixture was charged in an autoclave and reacted at an $H_2$ pressure of 100 kg/cm² and the corresponding temperature given in Table 6 for 20 hours. The reaction mixture was treated in the same manner as in Example 2 to determine the corresponding asymmetric ratio, R/S, and the yield of (the R form + the S form). Results are summarized in Table 6.

TABLE 6

| Solvent | Base | pH | Reaction temp. (20° C.) | R/S | (R + S Forms) yield (%) |
|---|---|---|---|---|---|
| Methanol | Benzyltri-methylammonium hydroxide | 12.68 | 20 | 13.2 | 86 |
| 1:1 Mixed solvent of methanol and water | Triethylamine | 11.47 | 0–5 | 13.1 | 83 |

EXAMPLE 5

To 2 ml of water or an organic solvent were added 20 mg of triacetyl-L-erythro-biopterin, 4 mg of platinum black and a base. The thus-prepared mixture was charged in an autoclave and reacted at an $H_2$ pressure of 100 kg/cm² and temperature of 20° C. for 20 hours. To the reaction mixture was added 2 ml of 3N hydrochloric acid, followed by removal of the catalyst through filtration. Concentrated hydrochloric acid (0.5 ml) was added to 1.5 ml of the filtrate and the resultant mixture was left over for 3 days to effect deacetylation. The thus-obtained reaction mixture was analyzed by high-pressure liquid chromatography under the same conditions as in Example 2 to determine the R/S ratio and the yield of (the R form and the S form). Results are summarized in Table 7.

TABLE 7

| Solvent | Base | pH | R/S | (R + S Forms) yield (%) |
|---|---|---|---|---|
| Water | Triethylamine | 11.72 | 9.0 | 68 |
| Water | Tetraethylammonium hydroxide | 12.05 | 7.4 | 72 |
| Water | Diethylamine | 12.03 | 7.4 | 70 |
| Water | Ethylamine | 12.01 | 12.7 | 87 |
| Methanol | Benzyltrimethyl-ammonium hydroxide | 12.63 | 9.4 | 65 |

EXAMPLE 6

To 95 ml of water were added 1.0 g (4.22 mmol) of L-erythro-biopterin and 0.20 g of platinum oxide, followed by an addition of 10% tetraethylammonium hydroxide to adjust the resultant mixture to pH 12.0. The thus-prepared mixture was charged in an autoclave and reacted with stirring, at an $H_2$ pressure of 100 kg/cm², temperature of 0°–5° C. and revolution rate of 1000 r.p.m. and for 20 hours. The reaction mixture was added with 5 ml of concentrated hydrochloric acid, followed by removal of the catalyst through filtration. The filtrate was then concentrated under reduced pressure at a bath temperature not higher than 35° C. The residue was recrystallized from ethanol. The crystalline matter was dissolved in 3N hydrochloric acid and the resultant solution was treated with activated carbon. The activated carbon was filtered off, the filtrate was concentrated, and the residue was recrystallized from a mixed solvent of 3N hydrochloric acid and ethanol to obtain 0.98 g of (6R)-BPH₄·2HCl as white crystals.

Elemental analysis: Calculated for $C_9H_{17}Cl_2N_5O_3$: C, 34.41; H, 5.45; N, 22.29. Found: C, 34.48; H, 5.53; N, 22.20.

Optical rotation $[\alpha]_D^{25}$: −6.51° (C, 0.68; 0.1N HCl)

$^1$H-NMR (CD₃OD+D₂O): 4.1–3.7 (5H, m, H-C(6,7,1',2')), 1.40 (3H, d, J=6 Hz, H-C(3')).

EXAMPLE 7

Water (2 ml), L-erythro-biopterin (20 mg), a catalyst (4 mg) and triethylamine were added to adjust the pH to 12. The thus-prepared mixture was charged in an autoclave and reacted with stirring, at an $H_2$ pressure of 100 kg/cm² and temperature of 0°–5° C. for 20 hours. To the reaction mixture was added 5 ml of concentrated hydrochloric acid, followed by removal of the catalyst through a microfilter. The filtrate was then analyzed by high-speed liquid chromatography to determine the asymmetric ratio, R/S, and the yield of (the R form + the S form). Results are summarized in Table 8.

Conditions for measurement by high-pressure liquid chromatography:

Detector: ultraviolet absorption photometer (measurement wavelength: 275 nm)

Column: Partisil-10SCX, 4.5×250 mm

Mobile phase: 30 mM ammonium phosphate plus 3 mM ammonium sulfite (pH=3.0)

Flow rate: 2 ml/min.

TABLE 8

| Catalyst | Asymmetric ratio, R/S | (R + S forms) Yield (%) |
|---|---|---|
| PtO₂ | 9.9 | 92 |
| 5% Pt/C | 8.6 | 81 |
| 5% Pt/alumina | 8.4 | 87 |
| PdO (comparison) | 3.3 | 14 |
| 5% Rh/C | 2.9 | 19 |

TABLE 8-continued

| Catalyst | Asymmetric ratio, R/S | (R + S forms) Yield (%) |
|---|---|---|
| (comparison) | | |

EXAMPLE 8

Using KOH, triethylamine, diethylamine, ethylamine and tetraethylammonium hydroxide as bases, the pHs of the reaction mixture were adjusted to 12 respectively. The procedure of Example 7 was repeated at 0° to 5° C. and an $H_2$ pressure of 100 kg/cm$^2$ by using $PtO_2$, 5% Pt/C and 5% Pt/alumina as catalysts respectively. Results are summarized in Table 9 to Table 11.

TABLE 9

| | PtO$_2$ | |
|---|---|---|
| | Asymmetric ratio, R/S | (R + S forms) yield (%) |
| Ethylamine | 8.1 | 89 |
| Diethylamine | 8.2 | 90 |
| Triethylamine | 9.9 | 94 |
| Tetraethylammonium hydroxide | 9.7 | 84 |
| KOH (comparison) | 5.5 | 83 |

TABLE 10

| | 5% Pt/C | |
|---|---|---|
| | Asymmetric ratio, R/S | (R + S forms) yield (%) |
| Diethylamine | 6.8 | 75 |
| Triethylamine | 8.6 | 81 |
| Tetraethylammonium hydroxide | 8.1 | 83 |
| KOH (comparison) | 4.1 | 88 |

TABLE 11

| | 5% Pt/alumina | |
|---|---|---|
| | Asymmetric ratio, R/S | (R + S forms) yield (%) |
| Triethylamine | 8.4 | 87 |
| Tetraethylammonium hydroxide | 8.0 | 82 |

EXAMPLE 9

The procedure of Example 7 was repeated except that platinum oxide was used as a catalyst, triethylamine was employed to adjust the pH to 12, and the reaction temperature and $H_2$ pressure were changed. Results are summarized in Table 12.

TABLE 12

| | H$_2$ pressure | | | | | |
|---|---|---|---|---|---|---|
| | 1 kg cm$^2$ | | 20 kg/cm$^2$ | | 100 kg/cm$^2$ | |
| Temperature | R/S | (R + S forms) yield (%) | R/S | (R + S forms) yield (%) | R/S | (R + S forms) yield (%) |
| 0–5° C. | 3.8 | 75 | 7.4 | 91 | 9.9 | 94 |
| 20° C. | 3.3 | 56 | 7.2 | 93 | 8.1 | 90 |
| 40° C. | 4.1 | 87 | 5.8 | 88 | 7.5 | 85 |

EXAMPLE 10

L-Erythro-biopterin (20 mg) and platinum oxide (4 mg) were added to each of the solvents shown in Table 13, followed by adjustment with the corresponding base given in the same table to the prescribed pH. The resultant mixture was charged in an autoclave and then reacted at an $H_2$ pressure of 100 kg/cm$^2$ and the corresponding temperature given in Table 13 for 20 hours. The reaction mixture was treated in the same manner as in Example 7 to determine the asymmetric ratio, R/S, and the yield of (the R form+the S form). Results are also given in Table 13.

TABLE 13

| Solvent | Base | pH | Temperature | R/S | (R + S Forms) yield (%) |
|---|---|---|---|---|---|
| Methanol | Benzyltrimethylammonium hydroxide | 12.6 | 20° C. | 8.7 | 85 |
| 1:1 Mixture of methanol and H$_2$O | Triethylamine | 11.5 | 0–5° C. | 7.9 | 82 |

EXAMPLE 11

To 2 ml of water or an organic solvent were added 20 mg of triacetyl-L-erythro-biopterin, 4 mg of platinum oxide and a base. In an autoclave, the thus-prepared mixture was reacted at an $H_2$ pressure of 100 kg/cm$^2$ and temperatures of 0° to 5° C. for 20 hours. The reaction mixture was added with 2 ml of 3N hydrochloric acid, followed by removal of the catalyst through filtration. Concentrated hydrochloric acid (0.5 ml) was added to 1.5 ml of the filtrate and the resultant mixture was left over for 3 days to effect deacetylation. The thus-obtained reaction mixture was analyzed by high-pressure liquid chromatography under the same conditions as in Example 7 to determine the R/S ratio and the yield of (the R form and the S form). Results are summarized in Table 14.

TABLE 14

| Solvent | Base | pH | R/S | (R + S Forms) yield (%) |
|---|---|---|---|---|
| Water | Triethylamine | 11.76 | 11.9 | 85 |
| Methanol | Benzyltrimethylammonium hydroxide | 12.52 | 8.2 | 88 |

Having now fully described the invention, it will be apparent to one of ordinary skill in the art that many changes and modifications can be made thereto without departing from the spirit or scope of the invention as set forth herein.

What is claimed as new and is secured by Letters Patent is:

1. A process for the preparation of (6R)-tetrahydro-L-biopterin, which comprises:
   hydrogenating L-erythro-biopterin or an acyl derivative thereof in the presence of an amine other than said biopterin starting material which controls the pH of the reaction medium to within the range of 10–13 and a platinum-based hydrogenation catalyst, and, in the event at least one acyl group remains in the hydrogenated biopterin product obtained,
   removing the acyl group by hydrolysis.

2. The process of claim 1, wherein the amine is selected from the group consisting of methylamine, ethylamine, propylamine, cyclohexylamine, dimethylamine, diethylamine, dipropylamine, piperidine, morpholine, trimethylamine, triethylamine, tripropylamine, tetramethylammonium hydroxide, tetraethylammonium hydroxide and tetrapropylammonium hydroxide.

3. The process of claim 1, wherein the hydrogenation is conducted under an elevated pressure of 10 to 100 kg/cm$^2$.

4. The process of claim 1, wherein the hydrogenation is conducted under an elevated pressure of 20 to 100 kg/cm$^2$.

5. The process of claim 1, wherein the platinum-based catalyst is selected from the group consisting of platinum black, platinum oxide, platinum/carbon and platinum/alumina.

6. The process of claim 1, wherein the platinum-based catalyst is platinum black.

7. The process of claim 1, wherein the hydrogenation is conducted in water, an alcohol or a mixed water-alcohol solvent.

8. The process of claim 7, wherein the alcohol is selected from the group consisting of methanol, ethanol, methyl cellosolve and ethylene glycol.

9. The process of claim 1, wherein the hydrogenation is conducted in water.

10. The process of claim 1 wherein the hydrogenation is conducted at a temperature in a range of from 31 10° C. to 50° C.

11. The process of claim 1, wherein the hydrolysis is conducted with hydrochloric acid.

* * * * *

UNITED STATES PATENT AND TRADEMARK OFFICE
CERTIFICATE OF CORRECTION

PATENT NO. : 4,713,454
DATED : DECEMBER 15, 1987
INVENTOR(S) : HIDEAKI SAKAI ET AL.

It is certified that error appears in the above-identified patent and that said Letters Patent is hereby corrected as shown below:

In claim 10, line 10, column 10, delete "from 31 10°C to 50°C" and insert --therefor from -10°C to 50°C--.

Signed and Sealed this

Twenty-first Day of May, 1991

Attest:

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,713,454

DATED : December 15, 1987

INVENTOR(S) : Hideaki Sakai et al

It is certified that error appears in the above-identified patent and that said Letters Patent is hereby corrected as shown below:

Claim 10, line 10, column 10, "therefor from -10°C" should read as --from -10°C--.

Signed and Sealed this

Second Day of March, 1993

Attest:

STEPHEN G. KUNIN

*Attesting Officer*     Acting Commissioner of Patents and Trademarks